(12) United States Patent
Skodda

(10) Patent No.: US 11,191,814 B2
(45) Date of Patent: Dec. 7, 2021

(54) PET FOOD FORMULATION WITH CANNABINOIDS

(71) Applicant: Anja Skodda, Venice, CA (US)

(72) Inventor: Anja Skodda, Venice, CA (US)

(73) Assignee: PAW POWER, INC., Venice, CA (US)

( * ) Notice: Subject to any disclaimer, the term of this patent is extended or adjusted under 35 U.S.C. 154(b) by 0 days.

(21) Appl. No.: 16/560,565

(22) Filed: Sep. 4, 2019

(65) Prior Publication Data

US 2020/0069776 A1 Mar. 5, 2020

Related U.S. Application Data

(60) Provisional application No. 62/726,467, filed on Sep. 4, 2018.

(51) Int. Cl.

| | |
|---|---|
| *A61K 38/39* | (2006.01) |
| *A61K 31/728* | (2006.01) |
| *A61K 31/7008* | (2006.01) |
| *A61K 31/375* | (2006.01) |
| *A61K 31/593* | (2006.01) |
| *A61K 31/355* | (2006.01) |
| *A23K 50/40* | (2016.01) |
| *A23K 20/147* | (2016.01) |
| *A23K 20/111* | (2016.01) |
| *A23K 20/121* | (2016.01) |
| *A23K 20/163* | (2016.01) |
| *A23K 20/174* | (2016.01) |

(52) U.S. Cl.
CPC ............ *A61K 38/39* (2013.01); *A23K 20/111* (2016.05); *A23K 20/121* (2016.05); *A23K 20/147* (2016.05); *A23K 20/163* (2016.05); *A23K 20/174* (2016.05); *A23K 50/40* (2016.05); *A61K 31/355* (2013.01); *A61K 31/375* (2013.01); *A61K 31/593* (2013.01); *A61K 31/7008* (2013.01); *A61K 31/728* (2013.01)

(58) Field of Classification Search
CPC .. A61K 38/39; A61K 31/728; A61K 31/7008; A61K 31/375; A61K 31/593; A61K 31/355; A23K 20/111; A23K 50/40; A23K 20/147; A23K 20/121; A23K 20/163; A23K 20/174
USPC ......................................................... 514/54
See application file for complete search history.

(56) References Cited

U.S. PATENT DOCUMENTS

| | | | |
|---|---|---|---|
| 9,826,760 B2 | 11/2017 | Ding et al. | |
| 2002/0025921 A1* | 2/2002 | Petito ..................... | A61K 38/39 514/25 |
| 2008/0003270 A1 | 1/2008 | Garcia Martinez | |
| 2011/0171187 A1* | 7/2011 | Moore ..................... | A61P 19/02 424/93.51 |
| 2014/0363537 A1 | 12/2014 | Doerr | |
| 2015/0132402 A1 | 5/2015 | Moore et al. | |
| 2016/0213027 A1 | 7/2016 | Maniatakos | |
| 2016/0303162 A1* | 10/2016 | Minatelli ........... | A61K 31/7008 |
| 2016/0316788 A1 | 11/2016 | Deveau-Greene et al. | |
| 2016/0376263 A1 | 12/2016 | Patron et al. | |

FOREIGN PATENT DOCUMENTS

| | | |
|---|---|---|
| CN | 105684931 A | 6/2016 |
| JP | 2016025870 A | 2/2016 |
| KR | 20060086396 A | 7/2006 |
| KR | 100889970 B1 | 3/2009 |
| WO | 2003034993 A3 | 5/2003 |
| WO | 2007148739 A1 | 12/2007 |
| WO | 2020060761 A2 | 3/2020 |

OTHER PUBLICATIONS

Glossary of medical education terms, Institute of International Medical Education. http://www.iime.org/glossary.htm Accessed in Mar. 2013 (Year: 2013).*
Jerosch J. Effects of Glucosamine and Chondroitin Sulfate on Cartilage Metabolism in OA: Outlook on Other Nutrient Partners Especially Omega-3 Fatty Acids. International Journal of Rheumatology vol. 2011, Article ID 969012, 17 pages. doi:10.1155/2011/969012 (Accepted Jun. 7, 2011) (Year: 2011).*
Ruff et al. Safety evaluation of a natural eggshell membrane-derived product. Food and Chemical Toxicology 50 (2012) 604-611. (Year: 2012).*
Written Opinion of the International Searching Authority, dated May 12, 2020, for corresponding PCT Application No. PCT/US19/49522, International Filing Date Sep. 4, 2019, consisting of 7 Pages.
International Search Report, dated May 12, 2020, for corresponding PCT Application No. PCT/US19/49522, International Filing Date Sep. 4, 2019, consisting of 2 Pages.
"Cannabis for Pets—Benefits and Dangers," Happy Dog Food Rawlicious Nutrition Blog, Jul. 8, 2016, Retrieved on May 30, 2020, Retrievable at: https://happydogfood.com/blogs/news/cannabis-for-pets-benefits-and-dangers.
Simone Fuchs, "Automated 3D cultivation of primary chondrocytes in the pannus model," BioSpektrum, Jan. 2004, pp. 693-694.
Michael Schunck, "The Effectiveness of Specific Collagen Peptides on Osteoarthritis in Dogs—Impact on Metabolic Processes in Canine Chondrocytes," Journal of Animal Sciences, 2017, 7, pp. 254-266.

* cited by examiner

*Primary Examiner* — Yih-Horng Shiao
(74) *Attorney, Agent, or Firm* — David Postolski, Esq.; Gearhart Law LLC

(57) ABSTRACT

A food supplement is disclosed that comprises an extracellular matrix composition of hydrolyzed collagen, hyaluronic acid and glucosamine, ascorbic acid and, optionally, a cannabinoid composition. The food supplement can be given to pet animals for the relief of or prophylaxis of degenerative joint diseases, such as arthritis.

10 Claims, 5 Drawing Sheets

| Ingredients | per 100 g | Explanation |
|---|---|---|
| Collagen hydrolysate (Origin pig) | 94 g | Collagen is listed in the revised feed material catalog EU VO 2017/1017. Description: Product based on protein from animal bones, skins, and tendons. Mandatory information: Crude protein, moisture, if > 8%. Subject to the requirements of Regulation (European Community) No 142/2011 (Annex VIII, Chapter III) for commercial and public health certificates of animal byproducts and derived products, and when using the catalog for identification purposes, please specify: the processed animal species (for example pig, ruminant, poultry, insect) and/or the life stage (for example larvae) and/or the processed material (for example bones) and/or the method used (e.g., degreased, refined). |
| Glucosamine hydrochloride | 5.9 g | Glucosamine (chitosamine) is listed in the revised feed material catalog EU VO 2017/1017. Description: Amino sugars (simple sugars) contained in the polysaccharides chitosan and chitin. They are obtained by hydrolysis of the exoskeleton of crustaceans and other arthropods or by fermentation of crops such as corn or wheat. Mandatory information: If necessary, sodium or potassium. In addition, the term "from animal tissue" or "from fermentation" must be given in the name. |
| Hyaluronic acid | 0.1 g of 0.105 g sodium hyaluronate | Hyaluronic acid is listed in the revised feed material catalog European Regulation 2017/1017.<br><br>Description: Glycosaminoglycan (polysaccharide) with repeating unit consisting of an amino sugar (N-acetyl-D-glucosamine) and D-glucuronic acid present in skin, synovial fluid and umbilical cord and for example from animal tissue or by bacterial fermentation is won. Mandatory information: If necessary, sodium or potassium. |
| Vitamin C | 30 mg as L-ascorbic acid | Vitamin C is listed in the European Union Register of Feed Additives (EC) No 1831/2003 with various compounds, Annex I (expiry date: 23.07.2025), regulated in detail by (European Union) Regulation 2015/1061. There is no mention of maximum or minimum quantity. |

FIG. 3

| Ingredients | per 100 g | Explanation |
|---|---|---|
| Vitamin E | 4,5 mg as d-alpha tocopheryl acetate | Vitamin E is listed in various compounds in the "European Union Register of Feed Additive as a Regulation (EC) No 1831/2003", Annex I (expiry date: 04.08.2025). Other forms (all forms with the exception of all-rac-alpha-tocopheryl acetate, RRR-alpha-tocopheryl acetate and RRR alpha tocopherol I) as vitamin E are listed under number 3a700 (expiry date 4.2.2021). Specifically regulated under European Union Regulation 26/2011 and its amendment European Union Regulation 2015/1747. There are not minimum or maximum amounts stated. |
| Vitamin D | 1.9 µg as cholecalciferol | Vitamin D is listed in various compounds in the "European Union Register of Feed Additive as a Regulation (EC) No 1831/2003", Annex I. For cholecalciferol, number 3a671, the following information applies: (expiry date 11.09.2027). Cholecalciferol is regulated in detail by the European Union Regulation 2017/1492. For "other animals", here dogs are referred to a maximum of 2 000 International Units or 0.05 mg/kg of complete feeding stuffs. |
| Palm oil | <0,1% | Vegetable oils and fats are listed in the revised feed material catalog EU VO 2017/1017. Description: Oils and fats derived from oilseeds or oilseeds (except castor oil). Products may be degummed, refined and/or hardened. Mandatory information: Humidity, if > 1%. The term "vegetable oils and fats" may optionally be replaced by the term "vegetable oil" or "vegetable fat". It is supplemented by the plant species and optionally by the part of the plant used. It is to be specified whether the oil (s) and/or fat (s) is/are crude or refined. |

FIG. 3 (continued)

Folium Biosciences
CERTIFICATE OF INTERNAL ANALYSIS

TYPE: PhytoCannabinoid-Rich Water Soluble Powder
BATCH No: COWSPA19-10
Date of Manufacture: 05Feb2019
Date of Analysis: 06Feb2019

POTENCY RESULTS:

| Cannabinoid | Wt. (%) | (mg/g) |
|---|---|---|
| CBD | 21.42 | 214.17 |
| CBG | <0.03 | <0.30 |
| CBN | <0.03 | <0.30 |
| THC | ND** | ND** |
| CBC | <0.03 | <0.30 |
| THC-A | ND** | ND** |
| CBD-A | <0.03 | <0.30 |
| MAX THC | ND** | ND** |
| MAX CBD | 21.42 | 214.17 |
| TOTAL ACTIVE | 21.42 | 214.17 |

Residual Solvents*

| Propane | Compliant with USP<467> | Pentane | Compliant with USP<467> |
|---|---|---|---|
| Isobutane | Compliant with USP<467> | Isopropanol | Compliant with USP<467> |
| Butane | Compliant with USP<467> | Hexane | Compliant with USP<467> |
| Ethanol | Compliant with USP<467> | Acetone | Compliant with USP<467> |

Heavy Metals*:

| Cadmium | Compliant with USP<233> |
|---|---|
| Lead | Compliant with USP<233> |
| Arsenic | Compliant with USP<233> |
| Mercury | Compliant with USP<233> |

TERPENE RESULTS*:

| | Wt. (%) | | Wt. (%) |
|---|---|---|---|
| β-Bisabolene | <0.1 | Camphene | <0.1 |
| β-Farnesene | <0.1 | E-Farnesene | <0.1 |
| Guaiol | <0.1 | Farnesol | <0.1 |
| β-Maaliene | <0.1 | α-Bisabolol | <0.1 |
| Calarene | <0.1 | P-Cymene | <0.1 |
| β-Caryophyllene | <0.1 | Linalool | <0.1 |
| α-Humulene | <0.1 | Myrcene | <0.1 |
| Cadinene | <0.1 | Phytol | <0.1 |
| α-Gurjunene | <0.1 | Isopulegol | <0.1 |
| d-Limonene | <0.1 | Terpinene | <0.1 |
| Nerolidol | <0.1 | Geraniol | <0.1 |
| α-Pinene | <0.1 | Myrcene | <0.1 |
| Aristolene | <0.1 | γ-Terpinene | <0.1 |
| Eucalyptol | <0.1 | δ-3-Carene | <0.1 |

Pesticides*:

| Acequinocyl | ND*** | Spinosad | ND*** |
|---|---|---|---|
| Pyrethrium | ND*** | Spirotetramat | ND*** |
| Spiromesifen | ND*** | Bifenazate | ND*** |
| Abamectin | ND*** | Fenoxycarb | ND*** |
| Imidacloprid | ND*** | Paclobutrazol | ND*** |

Test ID: 120318KP
*Batches are sent out regularly for testing, not all batches tested
**ND=Not Detected using a validated high-performance liquid chromatography test method
***Pesticides are tested by a third party lab, ND=Not Detected at the Reporting Limit (RL)
Batch Release:
Chemist: Sophia Alires       09Jan2019
Manager: Kathryn Sears       11Jan2019
(Updated 09Jan2019)

FIG.4

PET FOOD FORMULATION WITH CANNABINOIDS

CROSS-REFERENCE TO RELATED APPLICATIONS

This application claims the benefit of U.S. Provisional Patent Application 62/726,467, filed Sep. 4, 2018, the content of which is incorporated by reference herein in its entirety.

FIELD OF THE EMBODIMENTS

This invention relates to compositions and methods of using same for relieving the symptoms of degenerative joint disease in older domesticated animals and enhance growth in younger animals.

BACKGROUND OF THE EMBODIMENTS

As pets age they invariably suffer from degenerative joint disease, commonly known as arthritis. Certain breeds of dog like Labrador retrievers and German Shepherds even have a genetic predisposition to develop joint disease over time in their hips and elbows. The most common symptoms of arthritis include limping, reduced mobility, stiff spine, fatigue, irritability, muscle atrophy as well as persistent licking, chewing & biting of the affected area which can lead to skin inflammation and hair loss. A source of chronic, debilitating pain, arthritis undoubtedly produces a lot of discomfort for pets that severely diminishes their quality of life.

Arthritis can be triggered by joint instability resulting from ligament tears (e.g., the cranial cruciate ligament in the knee), bone fractures involving a joint, bone malformations, such as hip or elbow dysplasia, patellar luxations or a thickening of joint cartilage called Osteochondrosis dissecans (OCD). In other examples, arthritis stems from joint damage caused by infection or by joint inflammation caused by autoimmune diseases, such as lupus and rheumatoid arthritis. Whatever the cause, the ensuing damage to the joints results in the gradual atrophy of cartilage to a point where bone begins rubbing against bone creating chronic inflammation, swelling, excruciating pain, stiffness and a decreased range of motion. Moreover, this reduced mobility can lead to weight gain which adds further stress on the joints.

Although there is no cure for arthritis, the most common remedy is surgical intervention that is often prohibitively expensive and not without risk of complications such as infection.

Examples of related art are described below:

The published Korean Patent Applications KR1020060086396 and KR1020060006057 disclose cannabinoid receptor ligands for the treatment of diseases linked to the mediation of the cannabinoid receptors in animals.

The published Japanese Patent Application JP2016025870 discloses an edible polymer hydrogel orally administered prior to or during a meal for weight control and glycemic control.

The published International Patent Application WO2007/148739 discloses a cell activator, an anti-aging agent and an extracellular matrix production promoter, characterized by containing a plant extract containing a polyamine as an active ingredient in a cosmetic, a quasi-drug (such as an external preparation for skin, a bath agent or a hair growth agent), a food or drink or a pharmaceutical product.

The published U.S. Patent Application No. 2016/0376263 describes compounds and compositions known to modify the perception of bitter taste. Exemplary compositions comprise one or more of the following: cooling agents; inactive drug ingredients; active pharmaceutical ingredients; food additives or foodstuffs; flavorants, or flavor enhancers; food or beverage products; bitter compounds; sweeteners; bitterants; sour flavorants; salty flavorants; umami flavorants; plant or animal products; compounds known to be used in pet care products; compounds known to be used in personal care products; compounds known to be used in home products; pharmaceutical preparations; topical preparations; *cannabis*-derived or *cannabis*-related products; compounds known to be used in oral care products; beverages; scents, perfumes, or odorants; compounds known to be used in consumer products; silicone compounds; abrasives; surfactants; warming agents; smoking articles; fats, oils, or emulsions; and/or probiotic bacteria or supplements.

U.S. Pat. No. 9,826,760 discloses a collagen fiber reconstituted rawhide useful in the production of pet chews, and a method for making the same.

The published U.S. Patent Application No. 2016/0316788 discloses systems and methods for processing cattle ears into pet treats by high-pressure processing.

The published Chinese Patent Application CN105684931 discloses a collagen pet gel containing collagen fibers, collagen and auxiliary ingredients, wherein the collagen fibers and the collagen are extracted from animal skins.

The published U.S. Patent Application No. 2014/0363537 discloses a pet food product having a collagen casing with a filling material that contains at least one amylase.

None of the art described above addresses all of the issues that the present invention does. The pet food formulation disclosed herein comprises an enzymatically hydrolyzed collagen, hyaluronic acid, glucosamine, ascorbic acid, cannabidiol and a cannabinoid or prodrug thereof for alleviating at least one symptom of a degenerative joint disease.

SUMMARY OF THE EMBODIMENTS

A pet food formulation is disclosed that includes components of the extracellular matrix including hydrolyzed collagen, hyaluronic acid and glucosamine, together with ascorbic acid and a cannabinoid. The formulation can be given to pets for the treatment or prophylaxis of degenerative joint diseases such as arthritis.

In a first aspect, a method for alleviating at least one symptom of a degenerative joint disease in a non-human animal is disclosed comprising administering a food supplement consisting of an extracellular matrix composition comprising collagen, hyaluronic acid and glucosamine or a pharmaceutically acceptable salt thereof and a vitamin composition, wherein the formulation is effective at alleviating at least one symptom of a degenerative disease.

In a second aspect, a method for alleviating at least one symptom of a degenerative joint disease in a non-human animal is disclosed comprising administering a food supplement consisting of an extracellular matrix composition comprising collagen, hyaluronic acid and glucosamine or a pharmaceutically acceptable salt thereof, a vitamin composition, and a cannabinoid composition, wherein the formulation is effective at alleviating at least one symptom of a degenerative disease.

In certain embodiments of the first and second aspects, the at least one symptom of a degenerative joint disease comprises limping, reduced mobility, muscle atrophy or licking, chewing and/or biting of the affected joint.

In certain embodiments of the first and second aspects, the food supplement alleviates at least one symptom of a degenerative joint disease within a week of its administration.

In certain embodiments of the first and second aspects, the vitamin can be ascorbic acid.

In certain embodiments of the first and second aspects, the vitamin may further include vitamin D, vitamin E and/or coenzyme Q10.

In certain embodiments of the first and second aspects, the non-human animal can be a domesticated animal such as a dog, cat or horse.

In certain embodiments of the first and second aspects, the degenerative joint disease can be arthritis. The degenerative joint disease can be caused by joint instability.

In certain embodiments of the first and second aspects, the at least one symptom of a degenerative joint disease can be limping, reduced mobility, muscle atrophy or licking, chewing and/or biting of the affected joint.

In certain embodiments of the first and second aspects, the collagen can be a hydrolyzed collagen, such as a porcine collagen.

In a third aspect, a method for the prophylaxis of a degenerative joint disease in a non-human animal is disclosed comprising administering a formulation comprising hydrolyzed collagen, hyaluronic acid, glucosamine hydrochloride and ascorbic acid to the non-human animal.

In a fourth aspect, a method for the prophylaxis of a degenerative joint disease in a non-human animal is disclosed comprising administering a formulation comprising hydrolyzed collagen, hyaluronic acid, glucosamine hydrochloride, ascorbic acid and a cannabinoid or prodrug thereof to the non-human animal.

In a fifth aspect, a dietary supplement is disclosed comprising a therapeutically effective amount of a composition consisting of hydrolyzed collagen, hyaluronic acid, glucosamine hydrochloride and ascorbic acid, wherein the amount of the composition is effective at alleviating at least one symptom of a degenerative joint disease in a non-human animal.

In a sixth aspect, a dietary supplement is disclosed comprising a therapeutically effective amount of a composition consisting of hydrolyzed collagen, hyaluronic acid, glucosamine hydrochloride, ascorbic acid and a cannabinoid or prodrug thereof, wherein the amount of the composition is effective at alleviating at least one symptom of a degenerative joint disease in a non-human animal.

In certain embodiments of the fifth and sixth aspects, the non-human animal can be a dog, cat or horse.

In certain embodiments of the fifth and sixth aspects, the degenerative joint disease can be arthritis and the at least one symptom of a degenerative joint disease can be limping, reduced mobility, muscle atrophy or licking, chewing and/or biting of an affected joint.

BRIEF DESCRIPTION OF THE DRAWINGS

FIG. 3 shows the ingredients of an exemplary pet formulation.

FIG. 4 shows an exemplary phytocannabinoid-rich water soluble powder.

DESCRIPTION OF THE PREFERRED EMBODIMENTS

Figure 1:
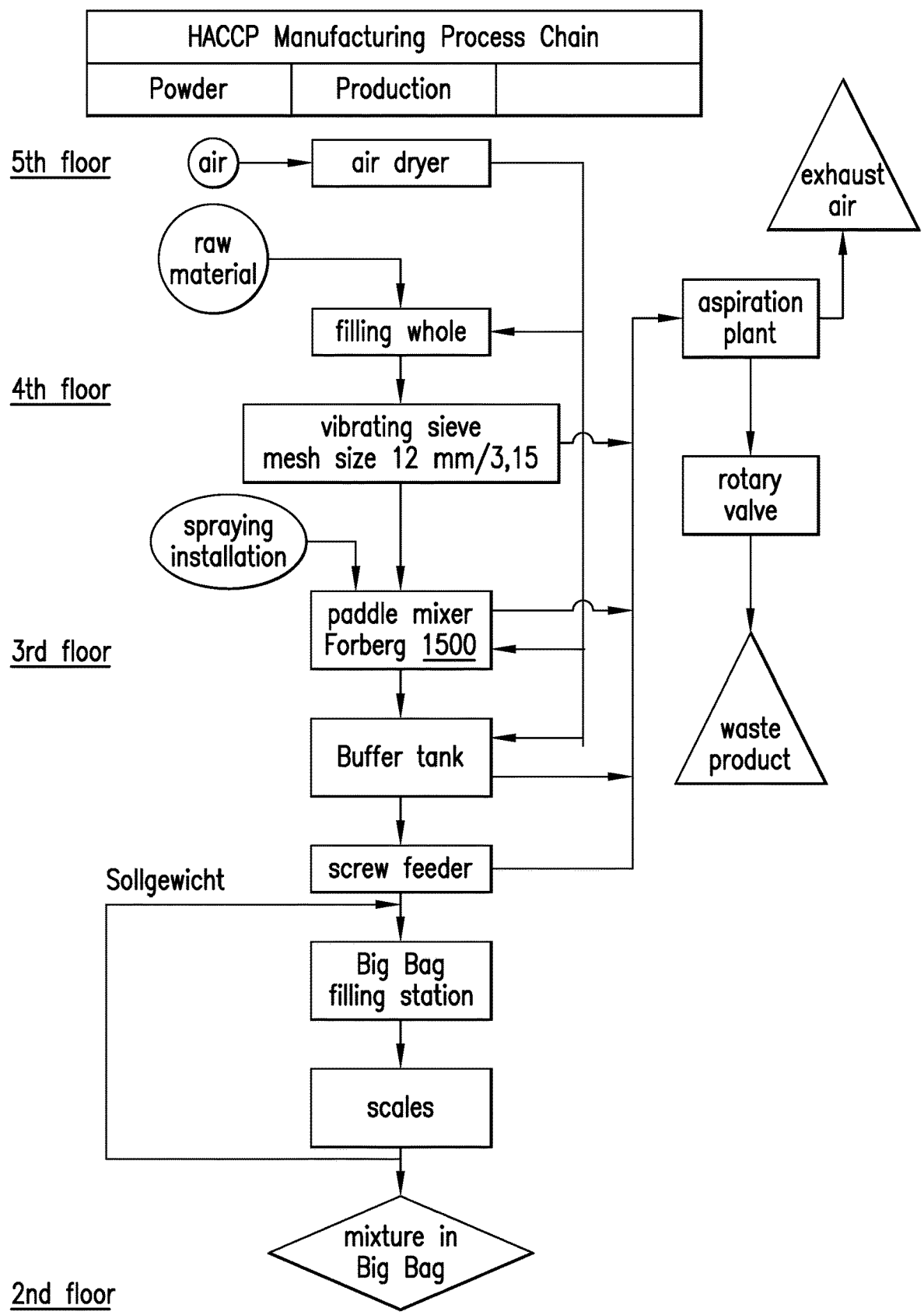
FIG. 1 shows an exemplary HACCP manufacturing process chain for the mixing of the ingredients of the disclosed pet food formulation.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4- 5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein, a pet food formulation or a pet food composition or a food supplement or food additive are used interchangeably throughout the specification and refer to the composition as described herein for the relief of symptoms associated with degenerative joint diseases in non-human animals. The supplement may be in any form, including solid (e.g. a powder), semi-solid (e.g. a food-like consistency/gel), a liquid or alternatively, it may be in the form of a tablet or capsule. The liquid can conveniently be mixed in with the food or fed directly to the animal, for example via a spoon or via a pipette-like device. The supplement may be high in one or more components of the invention or may be in the form of a combined pack of at least two parts, each part containing the required level of one or more component.

In certain embodiments, the disclosed pet food formulation can be in the form of a concentrate that is diluted prior to use.

In certain embodiments, the pet food formulation can be supplemented with a pharmaceutical composition, e.g. a medicament for the treatment of degenerative joint disease.

A pet food or foodstuff as disclosed herein encompasses any product that a non-human animal, such as a dog or cat, may consume in its diet. Thus, the disclosure covers standard food products, as well as pet food snacks (for example snack bars, biscuits and sweet products). The pet food or foodstuff is preferably a cooked product. It may incorporate meat or animal derived material (such as beef, chicken, turkey, lamb, blood plasma, marrowbone etc, or two or more thereof). The pet food or foodstuff alternatively may be meat free (preferably including a meat substitute such as soya, maize gluten or a soya product) in order to provide a source of protein.

The product may contain additional protein sources such as soya protein concentrate, milk proteins, gluten etc. The product may also contain a starch source such as one or more grains (e.g. wheat, corn, rice, oats, barley etc) or may be starch free. For example, a typical dry commercial dog and cat food contains about 30% crude protein, about 10-20% fat and the remainder being carbohydrate, including dietary fibre and ash. A typical wet, or moist product contains (on a dry matter basis) about 40% fat, 50% protein and the remainder being fibre and ash.

The term "therapeutically effective amount" as used herein refers to its meaning as is generally accepted in the art. The term generally refers to the amount of the pet food formulation that will elicit the requisite biological response in a non-human animal. For example, if a given treatment is considered effective when there is at least about a 25% reduction in a measurable parameter associated with a disease or disorder, a therapeutically effective amount of a drug for the treatment of that disease or disorder is that amount necessary to effect at least about a 25% reduction in that parameter.

The terms "administer," "administering," or "administration" are used herein in their broadest sense. These terms refer to any method of delivering a food supplement as described herein to a non-human animal. In a preferred embodiment, the food supplement is administered orally to a non-human animal.

Terms such as "treating," "treatment," "to treat," "alleviating," or "to alleviate" as used herein refer to both (1) therapeutic measures that cure, slow down, lessen symptoms of, and/or halt progression of a diagnosed pathologic condition or disorder (e.g., degenerative joint disease) and (2) prophylactic or preventative measures that prevent or slow the development of a targeted pathologic condition or disorder ("preventing" or "to prevent"). Thus, those non-human animals in need of treatment include those already with the disorder; those prone to have the disorder; and those in whom the disorder is to be prevented.

As used herein, the term "non-human animal" includes, but is not limited to, mammals, for example, domesticated animals such as pet animals or mammals kept in a zoo. Examples of pets or pet animals include dogs, cats, horses, sport horses and rodents, e.g., chinchillas, guinea pigs, degus, mice, gerbils, hamsters, rats, ferrets and lagomorphs, e.g., rabbits Animals of all ages are included, e.g. young, adults, animals of medium age and seniors. For example, the terms "domestic" dog and "domestic" cat mean pet dogs and cats, in particular, *Canis domesticus* and *Felis domesticus*.

Degenerative joint diseases include, but are not limited to, osteochondrosis, degenerative arthritis and arthropathy.

The degenerative joint disease, osteoarthritis, is a non-infectious progressive disorder of primarily the diarthrodial joints (e.g., the synovial weightbearing joints). The normal articular joint cartilage is smooth, white, and translucent. It is composed of cartilage cells (chondrocytes) embedded in a sponge-like matrix made of collagen, protein polysaccharides, and water. In osteoarthritis there is a progressive deterioration of articular cartilage characterized by hyaline cartilage thinning, joint effusion, and periarticular osteophyte formation. Joint degeneration can be caused by trauma, infection, immune-mediated diseases, or developmental malformations. The inciting cause initiates chondrocyte necrosis, release of degradative enzymes, synovitis, and continued cartilage destruction and inflammation. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density while any remaining cartilage begins to fray. Eventually, osteophytes (spurs of new bone) covered by cartilage form at the edge of the joint. As mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint disease is the result of mechanical instabilities or aging changes within the joint. This includes old age degenerative arthritis and, in younger animals, may be the result of injuries, bruises, abnormal joint configuration (i.e. hip dysplasia), or mechanical wear from anterior cruciate ligament rupture, patellar luxation, or osteochondritis dissecans. Degenerative joint disease can occur at any joint in an animal's body, including without limitation, knee, hip, shoulder, and spine.

Osteochondrosis is a disturbance in endochondral ossification that is sometimes classified as dyschondroplasia. It may involve the separation of the immature articular cartilage from the underlying epiphyseal bone, which sometimes dissects completely free and floats loose in the synovial cavity and results in accompanying synovitis, or it may result in the retention of pyramidal cores of physeal cartilage projecting into the metaphysis. Often, these two lesions occur simultaneously in the same bone. The disease occurs during maximal growth when the biomechanical stresses are greatest in the immature skeleton (4-8 months in dogs). It is most common in large and giant breeds of dogs and in rapidly growing pigs, horses (osteochondrosis), turkeys, and chickens.

Symptoms of degenerative joint disease include lameness, joint swelling, muscle atrophy, pericapsular fibrosis, and crepitation. Radiographic changes in the joint include joint effusion, periarticular soft-tissue swelling, osteophytosis, subchondral bone sclerosis, and possibly narrowed joint.

The disclosure describes a pet food formulation comprising, for example, a mixture of hydrolyzed collagen, hyaluronic acid and glucosamine, ascorbic acid and a cannabinoid composition to provide means of prevention and relief for non-human animals that are susceptible to develop, or that have already developed, a degenerative joint disease such as arthritis. The formulation facilitates the supply of nutrients to articular cartilage, promotes the biosynthesis of joint cartilage and attenuates chronic pain, joint inflammation and other symptoms caused by arthritis.

Extracellular Matrix Composition
Collagen

Hydrolyzed collagen protein, particularly enzymatically hydrolyzed collagen is described in U.S. Pat. No. 4,804,745 and the PCT application WO98/44929, the contents of which are incorporated herein by reference in their entireties. Hydrolyzed collagen is referred to as collagen hydrolysate, gelatine, gelatine hydrolysate, hydrolyzed gelatine, and collagen peptides. The process of hydrolysis involves breaking down the molecular bonds between individual collagen strands and peptides using combinations of physical, chemical or biological means. Typically, with skin-sourced collagen (Type-I collagens), hides are put in a lime slurry pit for up to 3 months, loosening collagen bonds; the hides are then washed to remove lime, and the collagen extracted in boiling water. The extracted collagen is evaporator concentrated, desiccated with drum driers, and pulverized. The amino acid content of hydrolyzed collagen is the same as collagen. Hydrolyzed collagen contains 19 amino acids, predominantly glycine, proline and hydroxyproline, which together represent around 50% of the total amino acid content. The bioavailability of hydrolyzed collagen in mice was demonstrated by orally administering 14C hydrolyzed collagen. Following digestion, more than 90% was absorbed within 6 hours, with measurable accumulation in cartilage and skin (see Oesser et al., Journal of Nutrition. (1999) 129 (10): 1891-1895).

In certain embodiments, the hydrolyzed collagen protein can have a molecular weight in the range of about 1 to about 300 kD. In certain embodiments, the hydrolyzed collagen protein can have a molecular weight of about 10, about 50, about 100, about 150, about 200, about 250 or about 300 kD.

In certain embodiments, the hydrolyzed collagen can have an average molecular weight of about 10, about 20, about 30, about 40, about 50, about 60, about 70, about 80, about 90 or about 100 kD. Higher molecular weight preparations are generally less readily soluble.

In a preferred embodiment, the hydrolyzed collagen is porcine collagen. Hydrolyzed porcine collagen powder is commercially available, e.g., from Summit Nutritionals. The powder has a particle size that passes through an 80-mesh sieve. It is 100% BSE free and comes from USDA approved sources.

In certain embodiments, the pet food formulation can contain about 1%, about 2%, about 3%, about 4%, about 5%, about 6%, about 7%, about 8%, about 9% or about 10% of hydrolyzed porcine collagen. In certain embodiments, the pet food formulation can contain 95%, 90%, 85%, 80%, 75%, 70%, 65%, 60%, 55%, 50%, 45%, 40%, 35%, 30%, 25%, 20%, 15%, 10%, 5% or less of hydrolyzed porcine collagen. In certain embodiments, the pet food formulation can contain about 99%, 98%, 97%, 96%, 95%, 94%, 93%, 92%, 91% or 90% w/w of hydrolyzed porcine collagen.

Glucosamine

Glucosamine and pharmaceutically acceptable salts thereof are commercially available, and are described in U.S. Pat. Nos. 5,587,363 and 5,364,845, the contents of which are incorporated herein by reference in their entireties. The primary source of exogenous glucosamine is the exoskeleton of shellfish and exists primarily in the form of glucosamine sulfate and glucosamine hydrochloride. Glucosamine and its pharmaceutically acceptable salts in combination with hydrolyzed collagen protein, provide the primary substrates for both collagen and proteoglycan synthesis including chondroitin sulfates and hyaluronic acid. In a preferred embodiment, the glucosamine is in a salt form so as to facilitate its delivery and uptake in the gastrointestinal tract after oral ingestion. The preferred salt form is glucosamine hydrochloride. A significant portion of the ingested glucosamine localizes to cartilage and joint tissues, where it remains for long time periods. This indicates that oral administration of glucosamine reaches connective tissues, where glucosamine is incorporated into newly-synthesized connective tissue.

The primary source of exogenous glucosamine is the exoskeleton of shellfish and exists in primarily two formulations, glucosamine hydrochloride (HCl) and glucosamine sulfate.

Glucosamine sulfate requires compound stabilizers in the form of salts and has 74% purity.

Glucosamine HCl lacks the sulfate group and has 99% purity. In a preferred embodiment, the pet food formulation comprises Glucosamine HCl.

Glucosamine administered orally is readily absorbed by the gastrointestinal tract. It is then rapidly metabolized by the liver and eliminated through the feces and urine. Peak levels in the bloodstream are achieved within about 8 hours after oral ingestion. Although the mechanism of action of glucosamine is unknown, recent studies suggest it may act as an anti-inflammatory agent that reduces the amount of nuclear factor kappa beta induced by interleukin-1 (IL-1).

In certain embodiments, the pet food formulation can contain about 1%, about 2%, about 3%, about 4%, about 5%, about 6%, about 7%, about 8%, about 9% or about 10% w/w of glucosamine hydrochloride. In certain embodiments, the pet food formulation can contain 1-10%, 1-20%, 1-30%, 1-40%, 1-50% of glucosamine hydrochloride.

Hyaluronic Acid

Hyaluronic acid, also known as hyaluronan, hyaluronate or sodium hyaluronate, is an abundant non-sulfated glycosaminoglycan that is present in all joint tissues. Hyaluronic acid is a naturally occurring linear polysaccharide composed of β1,4-linked D-glucuronic acid-((3-β1,3)-N-acetyl-D-glucosamine disaccharide units. In its native form, hyaluronic acid exists as a high molecular weight polymer (about 106-107 Da). In normal synovial fluid, the molecular weight of hyaluronic acid is between about $7 \times 10^6$ D to $7 \times 10^6$ Da, and the concentration is about 2-4 mg/ml.

Hyaluronic acid synthesized by synoviocytes is responsible for the viscoelastic properties of synovial fluid and plays a fundamental role in the maintenance of the trophic status of the cartilage.

In joint disease there is a reduction in both the concentration and molecular weight of hyaluronic acid. Inflammation oxidation stress enhances degradation of hyaluronan. Intra-articular injection of exogenous high molecular weight hyaluronic acid ($>5 \times 10^6$ Da) improves function in subjects with osteoarthritis or rheumatoid arthritis.

In certain embodiments, the pet food formulation can contain about 1%, about 2%, about 3%, about 4%, about 5%, about 6%, about 7%, about 8%, about 9% or about 10% of hyaluronic acid or pharmaceutically acceptable salts thereof.

In certain embodiments, the pet food formulation can contain about 0.1%, about 0.2%, about 0.3%, about 0.4%, about 0.5%, about 0.6%, about 0.7%, about 0.8%, about 0.9% or about 1% w/w of hyaluronic acid or pharmaceutically acceptable salts thereof.

Vitamin Composition

In certain embodiments, the food supplement may one or more vitamins, e,g, ascorbic acid, depending on the diet of the non-human animal. The concentration of the vitamins in the supplement may be used to "top up" the levels in the animal's diet or foodstuff. This can be done by including a quantity of the supplement with the animal's diet or by additionally feeding the animal a quantity of the supplement.

Vitamin C is a water-soluble substance and can be incorporated into the food supplement described herein (see published U.S. patent application 2003/0198661, the content of which is incorporated by reference herein in its entirety). Vitamin C is important for building cartilage, bones and teeth. It helps to strengthen and tighten the collagen fibers. Indeed, vitamin C is essential for producing the collagen structure.

The vitamin C composition may be in any form. It may be liquid, semi-solid or solid.

Preferably it is a heat stable. The source of the vitamin C is not limiting. Preferred vitamin C sources include crystalline ascorbic acid (optionally pure), ethylcellulose coated ascorbic acid, calcium phosphate salts of ascorbic acid, ascorbic acid-2-monophosphate salt or ascorbyl-2-monophosphate with small traces of the disphosphate salt and traces of the triphophate salt, calcium phosphate, or for example, fresh liver.

In certain embodiments, vitamin C can be in the form of trisodium L-ascorbic acid-2-monophosphate or sodium-calcium L-ascorbic acid-2-monophosphate both of which are commercially available, e.g. from DSM, Netherlands, under the tradename STAY-C®50 and STAY-C®35, respectively. In certain embodiments, these salts can be present in the food supplement at a concentration of from about 0.001% by weight to about 5% by weight, preferably in a concentration of from about 0.01% by weight to about 3% by weight, more preferably in a concentration of from about 0.1% by weight to about 1% by weight.

The preferred concentration of vitamin C is a level which preferably increases the plasma vitamin C level of an animal by up to about 25% (preferably 25% or more) in comparison with when the animal is fed a control diet.

In certain embodiments, the vitamin composition can further comprise vitamin E (e.g., D-alpha-tocopheryl acetate), vitamin D (e.g., cholecalciferol) and/or coenzyme Q10 (e.g. palm oil).

In certain embodiments, the pet food formulation can contain about 25, 50, 75, 100, 150, 200, 250, or 300 IU of vitamin D.

In certain embodiments, the pet food formulation can contain about 5, 10, 15, 20, 25, 30, 35, 40, 45, 50, 55, 60, 65, 70 or 75 mg of vitamin E (D-alpha-tocopheryl acetate).

In certain embodiments, the pet food formulation can contain about 0.1-1% palm oil.

Cannabinoid Composition

A cannabinoid is a class of chemical compositions that activate cannabinoid receptors, which may affect the behavior of neurotransmitters in the brain. Cannabinoid receptors are defined herein to include cannabinoid receptor type 1 (CB1), cannabinoid receptor type 2 (CB2), and the acetylcholine receptor AChR. Ligands for these receptor proteins include the endocannabinoids (produced naturally in the body by animals), the phytocannabinoids (found in *cannabis* and some other plants), and synthetic cannabinoids (manufactured artificially). The most notable cannabinoid is the phytocannabinoid tetrahydrocannabinol (THC), the primary psychoactive compound in *cannabis*. Cannabidiol (CBD) is another major constituent of the plant. There are at least 113 different cannabinoids isolated from *cannabis*, exhibiting varied effects. Phytocannabinoids may be found in *cannabis* and some other plants. Synthetic cannabinoids may be produced chemically. For example, a phytocannabinoid may be extracted from a plant including, but not limited to, *Cannabis sativa, Cannabis indica, Cannabis ruderalis, Echinacea purpurea, Echinacea angustifolia, Echinacea pallida, Acmella oleraca, Helichrysum umbraculigerum*, and *Radula marginata*.

Synthetic cannabinoids may encompass a variety of distinct chemical classes. These classes may include classical cannabinoids structurally related to tetrahydrocannabinol (THC). The synthetic cannabinoids may also encompass non-classical cannabinoids, such as cannabimimetics, including the aminoalkylindoles, 1,5-diarylpyrazoles, quinolines, and aryl sulphonamides as well as eicosanoids related to the endocannabinoids.

The most notable cannabinoid is the phytocannabinoid Δ9-tetrahydrocannabinol (THC), the primary psychoactive compound of *cannabis*. However, numerous other cannabinoids may be included in the composition with varied effects, including Δ8-tetrahydrocannabinol (THC), cannabidiol (CBD), cannabinol (CBN), and dodeca-2E,4E,8Z,10E/Z-tetraenoic-acid-isobutylamides are the most prevalent natural cannabinoids. Other common cannabinoids that may be used in the composition include, but are not limited to, cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM). The dodeca-2E,4E,8Z,10E/Z-tetraenoic-acid-isobutylamides and other cannabinoids may be derived from species in the *echinacea* genus.

Methods of transmucosally delivering a cannabinoid to an animal are described in, for example, the published U.S. Patent Application No. 2006/0257463, the content of which is incorporated by reference herein in its entirety.

Food Additives

Pet foods, particularly cat foods and dog foods, are commercially available in wet, dry, or semi-dry form, in various sizes and types of packaging. Food products designed for dogs, cats, or other household pets, are commonly made from meat, meat by-products, fish, fish by-products, cereals and grains and may also include vitamins and minerals. Typically such products are nutritious, but may not be highly savory or palatable. See, for example, the published U.S. Patent Application No. 2016/0213027, the content of which is incorporated by reference herein in its entirety.

Various methods and compositions are known for enhancing the palatability of pet foods by the addition flavorants or palatability enhancing compounds. U.S. Pat. No. 3,203,806 discloses enhancing the palatability of pet foods by the addition of a flavor-enhancing additive containing a small amount of acetamide and acetic acid. U.S. Pat. No. 4,070,490 discloses a pet food having the flavor and texture of animal liver prepared by a process that comprises heating a mixture of water, emulsified fat, reducing sugar and blood. U.S. Pat. No. 4,215,149 discloses a process for improving the palatability of particulate dry pet food by coating the surface of the particulates with fat and then applying a salt of phosphoric acid to the fat-coated surface. U.S. Pat. No. 4,267,195 discloses the addition of certain palatability enhancing compounds to dog foods. The compounds applied include L-proline, L-cysteine, L-histidine, L-lysine, inosine 5'-triphosphate, inosine 5'-diphosphate, and adenosine 5'-triphosphate. U.S. Pat. No. 4,393,085 discloses a process for the preparation of dog food wherein the palatability of the product is improved by treating a farinaceous component of the food with both protease and amylase enzymes. U.S. Pat. No. 5,186,964 discloses a method for increasing the palatability of dry cat food by the application of a surface coating of a sodium acid pyrophosphate, optionally together with an organic acid and a flavorant. U.S. Pat. No. 6,379,727 describes a flavoring system for pets that includes as its base maltodextrin with tricalcium phosphate and oleo-resin flavorings. The contents of each of these patents are incorporated by reference herein in their entireties.

Pet Food Formulation

The disclosed pet food formulation is not limited by the method of administering pet food formulation to a non-human animal. For example, the disclosed pet food formulation can be combined with an orally ingestible feed additive to form a supplement or premix that is added to pet food. For example, the disclosed pet food formulation can be added to a standard pet food or pet food additive in form of a broth or broth equivalent, a paste or as a lyophilized material. In some embodiments, the disclosed pet food formulation can be prepared as a fine particulate matter (e.g., having a particulate size of 0.25-0.5 mm, 0.125-0.250 mm, or 0.0625-0.125 mm in size, although larger and smaller particle sizes may also be used) that can be added to a pet food. The disclosed pet food formulation can be added to a carrier and/or encapsulated prior to addition to a pet food. In some embodiments, the disclosed pet food formulation (e.g., prepared as a fine particulate matter) is added directly to animal food (e.g., by sprinkling a liquid broth containing the composition over the pet food or by adding a dry particulate form of the disclosed pet food formulation to the pet food).

The disclosed pet food formulation is not limited by the amount (e.g., on a weight/weight percentage basis or on a volume/volume percentage basis) of the disclosed pet food formulation added to a pet food (e.g., total mixed ration). In some embodiments, the disclosed pet food formulation can be administered to a non-human animal as a proportion of total daily dry matter intake. For example, in some embodiments, the disclosed pet food formulation can be administered to an animal pet as 1.5%-2.5% of the subject's total daily dry matter intake, although lesser (e.g., 1.25%, 1.0%, 0.75%,0.5%, 0.25%, or less) and greater (e.g., 2.75%, 3%, 3.25%, 3.5%, 4%, or more) amounts of the disclosed pet food formulation may be administered.

Although this invention has been described with a certain degree of particularity, it is to be understood that the present disclosure has been made only by way of illustration and that numerous changes in the details of construction and arrangement of parts may be resorted to without departing from the spirit and the scope of the invention.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the packaging vectors, cell lines and/or methods of the invention may be made without departing from the spirit of the invention and the scope of the appended claims.

Example 1: Manufacture of Pet Food Supplement

Figure 2:
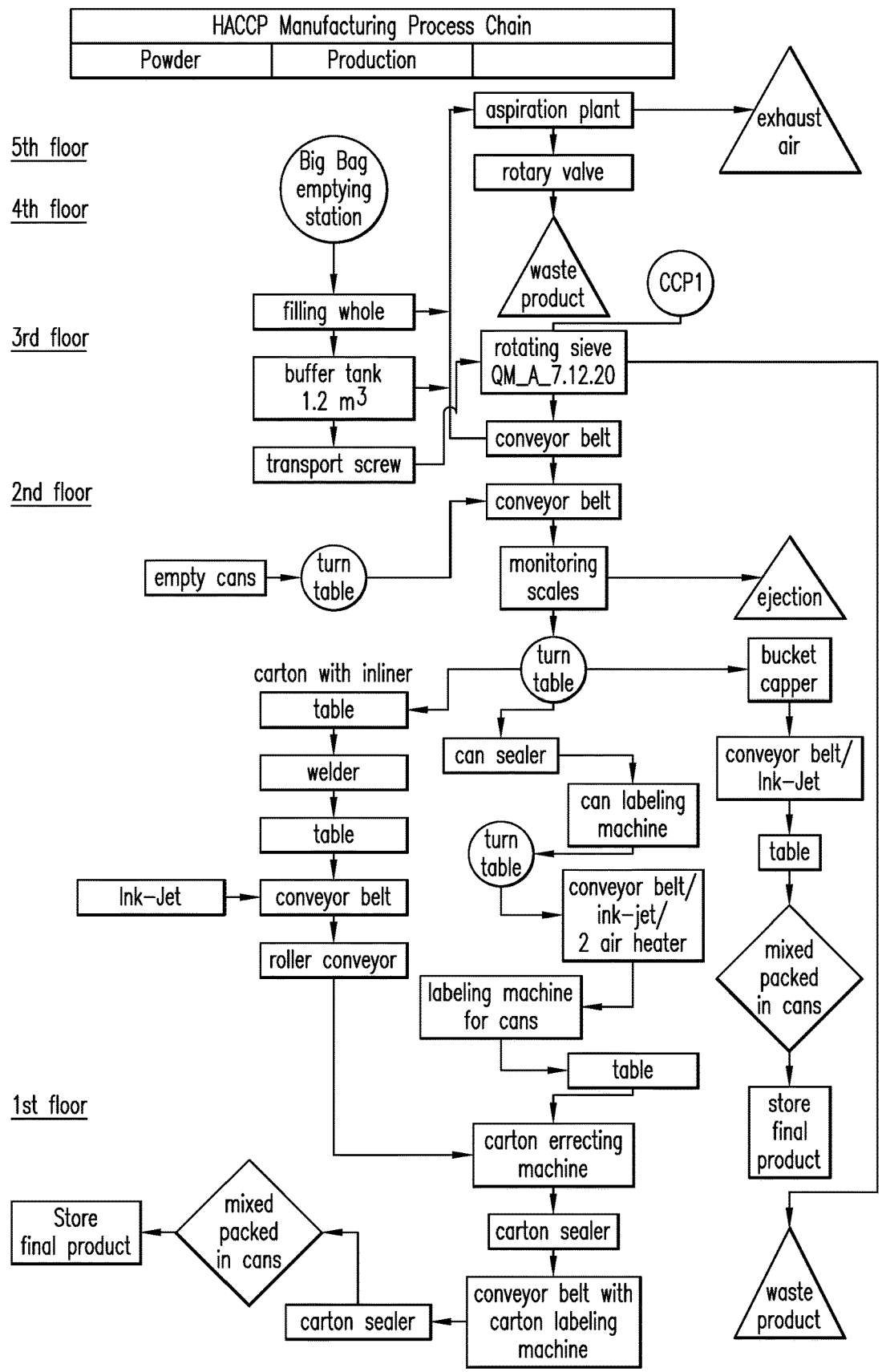
FIG. 2 shows an exemplary HACCP manufacturing process chain for final packaging of the disclosed pet food formulation.

The components of the food supplement are prepared as follows:
Hydrolysed Collagen (porcine) 94%
Glucosamine hydrochloride 5.9%
Sodium hyaluronate 0.1%
Palm oil (coenzyme Q10) 0.1%
Additives
Vitamin D as cholecalciferol 1200 I.E.
Vitamin E as D-alpha-tocopheryl acetate 4.5 mg
Vitamin C as L-ascorbic acid 30 mg The steps of the manufacture process are disclosed in FIGS. 1 and 2.

The ingredients of an exemplary pet food fsupplement are shown in FIG. 3.

The ingredients of an exemplary phytocannabinoid-rich water soluble powder is shown in FIG. 4.

Example 2: Pet Food Supplement for Dogs

The pet food supplement is supplied in packages of 400 g. For dogs weighing less than 10 kg, the daily regimen is 5 g of the food supplement taken orally/day, for dogs weighing less than 10-30 kg the daily regimen is 10 g of the food supplement taken orally/day, for dogs weighing less than 31-50 kg the daily regimen is 15 g of the food supplement taken orally/day and for dogs weighing more than 50 kg the daily regimen is 20 g of the food supplement taken orally/day.

The pet food supplement was given to a dog with symptoms of arthritis such as being unable to climb stairs because of the degenerative joint disease. Within 7 days of taking the pet formulation, the dog was able to climb stairs with ease.

What is claimed is:

1. A method for reducing a symptom of a degenerative joint disease in a non-human animal, comprising:
   administering to the non-human animal in need thereof a food supplement consisting of:

an extracellular matrix agent selected from the group consisting of: hyaluronic acid, hydrolyzed porcine collagen, and glucosamine or pharmaceutically acceptable salts thereof; and a vitamin selected from the group consisting of: vitamin D, vitamin E, vitamin C, and coenzyme Q10, wherein the food supplement is effective at reducing at least one symptom of the degenerative joint disease.

2. A method for reducing a symptom of degenerative joint disease in a non-human animal, comprising:

administering a food supplement to the non-human animal in need thereof, the food supplement consisting of:

an extracellular matrix agent selected from the group consisting of: hyaluronic acid, hydrolyzed porcine collagen,. and glucosamine or pharmaceutically acceptable salts thereof, a vitamin selected from the group consisting of: vitamin D, vitamin E, vitamin C, and coenzyme Q10, and a cannabinoid, wherein the food supplement is effective at reducing at least one symptom of a degenerative joint disease.

3. The method of claim 1, wherein the at least one symptom of the degenerative joint disease comprises limping, reduced mobility, muscle atrophy or licking, chewing and/or biting of an affected joint.

4. The method of claim 1, wherein the food supplement reduces the at least one symptom of the degenerative joint disease within a week of the administration.

5. The method of claim 1, wherein the non-human animal is a domesticated animal.

6. The method of claim 5, wherein the domesticated animal is a dog, a cat or a horse.

7. The method of claim 1, wherein the degenerative joint disease is arthritis.

8. The method of claim 7, wherein the at least one symptom of the degenerative joint disease comprises limping, reduced mobility, muscle atrophy or licking, chewing and/or biting of the affected joint.

9. A method for slowing development of a degenerative joint disease in a non-human animal, comprising:

administering a food supplement to the non-human animal in need thereof, wherein the food supplement consists of an effective amount of:

hydrolyzed porcine collagen, hyaluronic acid, glucosamine hydrochloride, coenzyme Q10, vitamin D, vitamin C, and vitamin E.

10. A method for slowing development of a degenerative joint disease in a non-human animal, comprising:

administering a food supplement to the non-human animal in need thereof, wherein the food supplement consists of an effective amount of: hydrolyzed porcine collagen, hyaluronic acid, glucosamine hydrochloride, coenzyme Q10, vitamin D, vitamin C, vitamin E, and a cannabinoid or prodrug thereof.

* * * * *